United States Patent
Pasechnik et al.

(10) Patent No.: US 6,660,264 B1
(45) Date of Patent: Dec. 9, 2003

(54) TREATMENT OF INTRACELLULAR INFECTION

(75) Inventors: Vladimir Artymovich Pasechnik, Salisbury (GB); Allen Douglas Glen Roberts, Southampton (GB); Richard James Sharp, Salisbury (GB)

(73) Assignee: Health Protection Agency, Salisbury (GB)

( * ) Notice: Subject to any disclaimer, the term of this patent is extended or adjusted under 35 U.S.C. 154(b) by 0 days.

(21) Appl. No.: 09/937,872

(22) PCT Filed: Apr. 10, 2000

(86) PCT No.: PCT/GB00/01350

§ 371 (c)(1),
(2), (4) Date: Nov. 20, 2001

(87) PCT Pub. No.: WO00/61190

PCT Pub. Date: Oct. 19, 2000

(30) Foreign Application Priority Data

Apr. 9, 1999 (GB) .............................................. 9908195

(51) Int. Cl.⁷ ........................ A61K 39/64; A61K 39/40; C12N 15/70; C12N 15/75; C12N 15/80
(52) U.S. Cl. .................. 424/93.6; 424/93.4; 424/93.21; 424/93.7; 424/205.1; 424/168.1; 424/248.1; 435/320; 435/2; 435/5; 435/7.22; 435/69.1; 435/91.31; 435/91.32
(58) Field of Search .............................. 424/93.6, 93.21, 424/93.4, 205.1, 248.1, 168.1, 93.7; 435/2, 5, 7.22, 320.1, 69.1, 91.32, 91.33

(56) References Cited

U.S. PATENT DOCUMENTS

| | | | |
|---|---|---|---|
| 5,547,932 A | 8/1996 | Curiel et al. | 435/65 |
| 5,693,509 A | 12/1997 | Cotten et al. | 435/172.3 |
| 5,789,230 A | 8/1998 | Cotten et al. | 435/235.1 |
| 5,922,859 A | 7/1999 | Birnstiel et al. | 536/24.5 |
| 5,965,404 A | 10/1999 | Buschle et al. | 435/69.52 |
| 6,121,036 A | 9/2000 | Ghanbari et al. | 435/235.1 |
| 6,284,880 B1 | 9/2001 | Cotten et al. | 536/23.5 |

FOREIGN PATENT DOCUMENTS

| | | |
|---|---|---|
| GB | 829266 | 3/1960 |
| WO | WO 90/02809 | 3/1990 |
| WO | WO 90/12095 | 10/1990 |
| WO | WO 90/12096 | 10/1990 |
| WO | WO 91/17773 | 11/1991 |
| WO | WO 92/01047 | 1/1992 |
| WO | WO 92/06180 | 4/1992 |
| WO | WO 92/06191 | 4/1992 |
| WO | WO 92/15605 | 9/1992 |
| WO | WO 92/15677 | 9/1992 |
| WO | WO 92/15679 | 9/1992 |
| WO | WO 92/17210 | 10/1992 |
| WO | WO 92/19281 | 11/1992 |
| WO | WO 92/20791 | 11/1992 |
| WO | WO 93/00103 | 1/1993 |
| WO | WO 94/24959 | 11/1994 |
| WO | WO 95/27043 | 10/1995 |
| WO | WO 96/00294 | 1/1996 |
| WO | WO 96/21007 | 7/1996 |
| WO | WO 97/23608 | 7/1997 |
| WO | WO 97/29185 | 8/1997 |
| WO | WO 97/39111 | 10/1997 |
| WO | WO 98/05344 | 2/1998 |
| WO | WO 99/10014 | 3/1999 |
| WO | WO 99/10485 | 3/1999 |
| WO | WO 00/53163 | 9/2000 |

OTHER PUBLICATIONS

Mc Nerney et al. Int. J. Tuberc. Lung Dis. 1999, vol. 3, pp. 179–184.*
Lederberg Proc. Natl. Acad. Sci. USA, 1996, vol. 93, pp. 3167–3168.*
Soothill J.S. J. Med. Microbiol. 1992, vol. 37, pp. 258–261.*
Sula Czechoslovak Medicine 1981, vol. 4, pp. 209–214.*
Curiel, D.T., et al., "Adenovirus enhancement of transferrin–polylysine–mediated gene delivery," *Proc. Natl. Acad. Sci. USA* 88: 8850–8854, National Academy of Sciences (1991).
Larocca, D., et al., "Targeting Bacteriophage to Mammalian Cell Surface Receptors for Gene Delivery," *Hum. Gene Ther.* 9:2393–2399, M.A. Liebert (1998).
International Search Report for PCT/GB00/01350.

* cited by examiner

Primary Examiner—James Housel
Assistant Examiner—Bao Qun Li
(74) Attorney, Agent, or Firm—Sterne, Kessler, Goldstein & Fox P.L.L.C.

(57) ABSTRACT

An agent for combating an intracellular microbial infection comprises a phage component and, associated therewith, a targeting moiety which directs the agent to a target cell and initiates delivery of the phage into the target cell. Once inside the target cell, the phage causes lysis of a microorganism residing within the target cell. A mycobacteriophage is combined with a targeting moiety of transferrin. Compositions comprising the agent, methods of preparing said agent, and use of said agent for combating intracellular infections are also provided.

10 Claims, No Drawings

TREATMENT OF INTRACELLULAR INFECTION

The present application is a 371 of PCT/GB00/01350 filed on Apr. 10, 2000, and published in English on Oct. 19, 2000, the disclosure of which is incorporated herein by reference in its entirety.

The present invention relates to an agent for causing lysis of a microorganism residing within a cell, to a method for preparing said agent, to compositions comprising said agent, and to the use of said agent. In particular, the agent of the present invention is suitable for the treatment of an intracellular infection by a microorganism.

Many microorganisms are capable of forming intracellular infections. These include: infections caused by species of Salmonella, Yersinia, Shigella, Campylobacter and Chlamydia. Live Salmonella and Yersinia can survive within the cells of mucosa of the gastrointestinal tract and fibroblasts, provide antigenic material continuously into the blood circulation and stimulate chronic inflammation and lead to arthritis; infections caused by the survival of *Legionella pneumophila* within alveolar macrophages and epithelial cells; infections caused by the survival of *Listeria monocytogenes* within cell cytosol; infections caused by an intracellular protozoan *Toxoplasma gondii*; and infections caused by the intracellular survival of Bordetella species (macrophages), *Staphylococcus aureus* (epithelial cells) and Group B streptococci (macrophages). Some of these infections are exclusively intracellular, others contain both intracellular and extracellular components. However, it is the intracellular survival cycle of bacterial infection which is suspected as a main supportive factor for disease progression.

Generally, these microorganisms do not circulate freely in the body, for example, in the bloodstream. Accordingly, intracellular microorganisms are often not amenable to drug treatment regimes. Where drugs are available, this problem has been exacerbated by the development of multiple drug resistant. microorganisms. For similar reasons, vaccine therapies are not effective against such intracellular microorganisms. Also, increased systemic concentration of antibiotics to improve bioavailability within cells may result in severe side effects.

As an example of an intracellular disease-causing microorganism, reference is made to *Mycobacteria tuberculosis*. This bacterium is responsible for causing the disease tuberculosis which is responsible for more than three million deaths a year world-wide. *M. tuberculosis* infects macrophage cells within the body. Soon after macrophage infection, most *M. tuberculosis* bacteria enter, persist and replicate within cellular phagosome vesicles, where the bacteria are sequestered from host defenses and extracellular factors.

A number of drug therapy regimes have been proposed for combating *M. tuberculosis* infections, with the best results to date having been achieved with the drug isoniazid. As an alternative, bacteriophage therapy has been suggested in the early 1980's based on results of the treatment of experimental tuberculosis with rabbits infected with *M. bovis* BSG and *M. microti*, and guinea pigs infected with the human pathogen *M. tuberculosis* strain H37Rv. However, the highest therapeutic effect obtained with bacteriophage was not higher than that achieved with isoniazid.

Phage, in particular bacteriophage, have been known for many years and have been employed as delivery vehicles in conventional treatment regiments for alleviating conditions associated with defective or aberrant cells.

For example, WO 98/05344 teaches the use of bacteriophage for delivering an exogenous gene, such as a therapeutic polynucleotide, to a mammalian cell. Targeting of the bacteriophage to a pre-selected cell is achieved by use of a targeting moiety linked to the bacteriophage, said targeting moiety effecting binding and initiating internalisation of the bacteriophage into the pre-selected cell. Once delivered to the pre-selected mammalian target cell, the exogenous genetic material can be transcribed and translated, thereby increasing the concentration of the therapeutic molecule encoded by the therapeutic polynucleotide in the target cell.

Aberrant cell treatment regiments such as those disclosed in WO 98/05344 are conventionally known as gene therapy methods. Such regiments, however, do not address the problem and/or persistence of intracellular infections by microorganisms.

WO 97/29185 teaches the preparation of recombinant phages, and the use thereof in the treatment or prophylaxis of bacterial infections. According to WO 97/29185, an anti-bacterial antibody is presented from an exposed surface of a bacteriophage, thereby rendering the bacteriophage capable of binding to and inhibiting growth of the targeted bacterial cell. WO 97/29185 does not, however, teach how to combat intracellular infections by microorganisms.

Additional background art relating to modified bacteriophage is provided in:

WO 99/10485, which teaches a bacteriophage system for identifying ligands susceptible to cell internalisation. Such ligands may provide suitable targets for bacteriophage gene delivery vehicles; and WO 94/24959, which teaches a method of detecting compounds by utilising a chemically modified lambdoid bacteriophage. In more detail, a bacteriophage is modified to form a phage-target molecule complex, said complex being non-infective. Upon challenge with a molecule of interest, the target molecule is cleaved and the bacteriophage becomes infective. Thus, the presence of a molecule of interest may be detected by the presence of infective bacteriophage.

Neither of WO 99/10485 or WO 94/24959 addresses problems associated with microbial infections, least of all the problem of combating intracellular microbial infections.

There is therefore a need for a system for combating intracellular infections by microorganisms. In particular, there is a need for a system for combating intracellular infections by mycobacteria.

The above problem is alleviated by the present invention which, according to a first aspect, provides an agent for causing lysis of a microorganism residing within a target cell, comprising a targeting moiety capable of binding to a target cell and a phage associated with the targeting moiety, wherein following binding of the targeting moiety of the cell the phage enters the target cell and effects lysis of the microorganism residing within the target cell.

The term "targeting moiety" means any structure which is capable of binding to the cell of interest. Examples include an antibody or fragment thereof, a receptor capable of binding to a ligand on the cell of interest, and a ligand capable of binding to a receptor on the cell of interest. Preferably, the targeting moiety is a ligand for a cell-surface receptor. Good results have been achieved in a specific embodiment of the invention using a transferrin molecule as targeting moiety. The targeting moiety need not demonstrate 100% specificity for the cell of interest, though naturally a degree of specificity is desirable for a highly efficient system. The targeting moiety may be capable of binding and internalisation, in which case the phage and targeting moiety may be delivered as a complex (ie. associated) into the target cell. Identification of potential targeting moieties susceptible to internalisation may be achieved by, for example, conventional methods such as those disclosed in WO 99/10485, or on a trial-and-error basis. Alternatively, the targeting moiety may be capable of binding but not internalisation, in which case the phage alone may be delivered into the target cell.

The term "binding" includes any interaction between the targeting moiety and the cell of interest which permits the phage to be delivered into the cell. This delivery process is one in which the whole phage enters the cell of interest. The targeting moiety may become separated from the phage during this delivery process. Without being bound by any theory, it is believed that binding involves the formation of a complex between the agent and a receptor present on the target cell. It is believed that formation of the complex induces internalisation of the agent via a receptor-mediated delivery mechanism such as that utilised by native eukaryotic viruses (eg. adenovirus).

The term "associated" means any interaction between the targeting moiety and the phage such that the targeting moiety is capable of directing the phage to the cell of interest and when so directed the phage may be delivered into the cell. Any one phage may be associated with one or more targeting moieties. Where a given phage is associated with more than one targeting moiety, each such moiety may bind to a different cell-type. Alternatively, each targeting moiety preferably binds to the same cell-type, although each may recognise a different site on the same cell-type.

The term "lysis" is used in this specification to include destruction of the microorganism through damage to or rupture of the microorganism cell wall. However, it is also intended to include any phage action which causes arrested growth and/or multiplication of the intracellular microorganism. In contrast to the phage of the present invention, which are employed to combat intracellular microbial infections by effecting lysis of the microorganism in question, the prior art bacteriophage vectors employed in gene therapy regiments are non-lytic towards microorganisms. Conventional gene therapy bacteriophage vectors are non-lytic towards microorganisms to ensure that the natural bacterial flora of a mammalian host are unaffected by the bacteriophage during gene transfer treatment regiments. In this respect, conventional gene therapy bacteriophage are often rendered abortive to lytic growth prior to use in gene therapy regiments. This may be achieved, for example, by modifying bacteriophage tail proteins that are required for natural phage transduction so that the bacteriophage is non-functional in a prokaryotic host, or by otherwise rendering the bacteriophage incapable of mediating injection of genetic material into a eukaryotic host cell. In contrast, the phage of the present invention are capable of natural phage transduction and of effecting lysis of a microorganism.

Reference to phage throughout this specification includes recombinant phage and derivatives thereof which are capable of causing lysis of a microorganism.

In operation of a specific embodiment of the invention, described below in more detail, the targeting moiety is a ligand for a cell-surface receptor and is physically or chemically associated with a phage. This phage-targeting moiety combination is administered to cells infected by an intracellular microorganism and the phage enters the cells and lyses microorganism within those cells. In the case that the microorganism is located within an intracellular compartment or vesicle the phage may also enter that internal compartment or vesicle. It is further preferred that the targeting moiety binds to an internal compartment or vesicle in the cell and within which the microorganism can reside. Thus, the targeting moiety may be a ligand for a cell surface receptor and also a ligand for a receptor on the surface of an internal compartment or vesicle. Following internalisation of the phage into a target cell, the presence of a targeting moiety for a receptor on the surface of an internal compartment or vesicle facilitates entry of the phage into the internal compartment or vesicle where, once inside, it may exert a lytic effect on the microorganism residing within the internal compartment or vesicle.

The targeting moiety for a cell surface receptor and the targeting moiety for a receptor on the surface of an internal compartment or vesicle may be the same or different. In the latter embodiment, the agents of the present invention may be modified such that the targeting moiety for the receptor on the internal compartment or vesicle is functional only following entry of the phage into a target cell. This may be achieved, for example, by employing a cell-specific promoter to ensure that the targeting moiety for the receptor on the surface of the internal compartment or vesicle is expressed only after the phage has been delivered to that specific cell-type. Alternatively, the targeting moiety for the receptor on the surface of the internal compartment or vesicle may be obscured (eg. by steric hindrance) on the surface of the phage prior to use thereof in accordance with the present invention. However, the targeting moiety for the receptor on the surface of the internal compartment or vesicle may be made accessible (eg. by cleavage or other modification of the targeting moiety for the cell surface receptor) during the internalisation process following binding of the agent to the target cell.

In one embodiment of the present invention, once the phage of the present invention has been delivered to the target cell of interest it remains as a separate entity and does not (or any part thereof) integrate into the target cell's genome.

In another embodiment, the phage contains substantially no exogenous (ie. non-phage) nucleic acid. In a further embodiment the phage contains substantially no exogenous nucleic acid other than that coding for the targeting moiety.

In one embodiment, the phage comprises substantially no exogenous therapeutic polynucleotides capable of mediating a therapeutic benefit in a recipient of the polynucleotide or product thereof. A "therapeutic polynucleotide product" refers to a molecule produced as a result of transcription or translation of the therapeutic polynucleotide. Therapeutic polynucleotide products include transcription products (eg. antisense mRNA and catalytic RNA), and translation products (eg. proteins or peptides) of the therapeutic polynucleotide.

The targeting moiety may be chemically linked to the phage. This may be achieved, for example, via a linker molecule (eg. a short peptide) or by other covalent means, for example, via a disulphide bridge. The targeting moiety may be bound to any part of the phage. The fusion between a targeting moiety and a phage should impair neither the binding of the targeting moiety to the cell membrane receptor nor the binding of the phage to its bacterial receptor. In relation to the targeting moiety, the chemical linkage procedure should not significantly alter the binding site to the cell receptor, e.g. by altering its conformation or by imposing structural rigidity. The transferrin chemical linkage illustrated in the present application does not prevent its binding to its receptor. The selected targeting moiety preferably demonstrates conformational stability. The chemical linkage construct preferably places the targeting moiety at a distance from the phage body sufficient to provide the targeting moiety with a degree of rotational flexibility so as to preserve maximum interaction of the targeting moiety with its receptor. The preferred means for chemical linkage is heterofunctional crosslinking via a disulfide bridge.

Alternatively, the targeting moiety may be physically mixed with the phage. In this case, the target moiety may become physically adsorbed to the phage by, for example, hydrogen-bonding, hydrophobic/hydrophilic bonding, van der Waal's forces, electrostatic forces or other charged associations. For example, the phage may carry a negative surface charge and the targeting moiety would then preferably carry a positive surface charge. Alternatively, at the selected pH (eg. pH 7–8, preferably approximately pH 7.5) the phage carries a positive charge sufficient to bind to a more negatively charged targeting moiety.

There are several ways of chemical linking of a targeting moiety to the phage via a disulfide bridge, examples of which are given below. Whilst transferrin (Tf) is illustrated below as the targeting moiety, the same linking means are equally applicable to other types of targeting moiety.

One embodiment is first to introduce free sulfhydril groups (—SH) in the transferrin molecule which does not have such groups in its native state. This can be done, eg. by thiolation of one or more free amino groups of the transferrin molecule with a reagent (eg. 2-iminothiolane) which modifies these groups and introduces —SH groups at these positions (this leads to Tf—SH). By changing the ratio of transferrin to 2-iminothiolane, temperature and pH of the reaction, modification can be achieved that will not impair transferrin binding to its receptor. Preferably 5–10 SH groups per Tf molecule are so modified. Then modified transferrin is purified from the low molecule weight reagent by gel filtration, eg. with Sephadex G-50 column and concentrated to about 1–3 mg/ml over a microfiltration membrane with a 30 kDa cut-off.

The phage is pre-treated by mixing with a heterobifunctional cross-linking agent (eg. Sulfo-SMCC, sulphosuccinilimidyl 4-(N-maleimidomethyl)-cyclohexane-1-carboxylate) which covalently binds to free-$NH_2$ groups on the phage, leaving in the solution phage having active maleimide groups which are able to react with a —SH group from the thiolated transferrin. The degree of phage modification may be controlled by the ratio of the crosslinking agent to phage. This reaction should take place preferably at a temperature in the interval 4–15° C. to preserve phage stability and to provide a good rate of modification. At the end of the reaction, modified phage is isolated from the reaction mixture by gel filtration on Sepharose 6B column and concentrated by membrane filtration.

At the next step, Tf—SH is mixed with an activated phage and the product (Tf-S-S-linker-Phage) is again isolated from Tf—SH by gel filtration in the same column. The presence of non-reacted phage can be afforded since it can only enhance the biological activity of the final preparation.

Another strategy of developing Tf-S-S-linker-Phage product can involve the activation of Tf free —NH2 groups and cross-linking activated transferrin with —SH groups at the phage surface. The outcome of this process depends on the availability and accessibility of —SH groups at the phage surface.

The formation of Tf-phage physical aggregate depends mainly on their electrostatic charge at the pH of the mixture (this is' preferably taken as a physiological pH).

The present invention has application in the treatment of any microorganism within a cell. In use of the invention, a phage capable of lysing the microorganism is identified and associated with a targeting moiety capable of directing the phage to the infected cell, preferably to a specific compartment of the infected cell which contains an infectious agent.

Thus, the agent of the present invention may be employed to treat an intracellular infection by a virus or by a bacterium. In one embodiment, this may be achieved by selection of a targeting moiety which is the same as the receptor employed by the infectious agent of interest. The agent of the present invention would then follow the same intracellular route as the infectious agent. By way of example, complement receptors CR1 and CR3 are known as a gate for *M. tuberculosis* infection and therefore complement components such as C2a and C3B are targeting moiety candidates for phage modification. Another candidate which can be internalised via CR3 is *Bordetella pertussis* haemaglutinin. Another group of targeting moieties comprises those used by infectious agents during their intracellular persistence and/or which are required for their replication. Transferrin is one example of such a moiety. This protein is required for providing *M. tuberculosis* with iron which is critical for the bacterium's intracellular survival.

The present invention is suitable for treating a number of intracellular infections. These include infections caused by Salmonella, Yersinia, Shigella, Campylobacter and Chlamidia. Live Salmonella and Yersinia can survive within the cells of mucosa of the gastrointestinal tract and fibroblasts, provide antigenic material continuously into the blood circulation and stimulate chronic inflammation and lead to arthritis. Also infections caused by the survival of *Legionella pneumophila* within alveolar macrophages and epithelial infections caused by the survival of *Listeria monocytogenes* within cell cytosis infections caused by an intracellular protozoan *Toxoplasma gondii*, and infections caused by the intracellular survival of Bordetella species (macrophages), *Staphylococcus aureus* (epithelial cells) and Group B streptococci (macrophages). Some of these infections are exclusively intracellular, others contain both intracellular and extracellular components. However, it is the intracellular survival cycle of bacterial infection which is suspected as a main supportive factor for disease progression.

The present invention is also applicable for suppression of intracellular persistence, for example, within macrophages of other bacteria such as *Leishmania donovani, Legionella pneumophila, Bordetella pertussis* and other species of bordetellae, Group B streptococci, *Salmonella* species, *Chlamydia* and *Borrelia burgdorferi*. This can be achieved with the use of the macrophage-specific delivery moiety and a lytic bacteriophage specific for the microorganism.

The present invention maybe used against intracellular viruses. There maybe an advantage in using a targeting moiety linked eg. to an antibody to a specific viral protein or to a short anti-sense DNA fragment. Such fusion construction may be delivered into a target cell as described previously.

Where the microorganism is a bacterium, the phage for use in the agent of the present invention is a bacteriophage. Bacteriophages are phages which parasitise bacteria. They typically comprise a head containing genetic material (usually DNA; though occasionally RNA), enclosed by a wall of protein which is usually prolonged into a hollow tail. A bacteriophage initiates infection by attaching itself by its tail to the wall of a bacterial cell. Through enzyme action, the wall is perforated and bacteriophage genetic material passes through and into the bacterial cell. The bacteriophage genetic material then organises the bacterium to make more bacteriophage genetic material which assembles with bacteriophage head and tail to form assembled particles. These assembled particles are then released by lysis of the host bacterial cell. Bacteriophage are typically highly specific, with each kind of bacteriophage typically infecting only one bacterial species or strain.

In one embodiment, the bacteriophage is preferably a lytic bacteriophage.

Preferably the bacteriophage is a mycobacteriophage. The mycobacteriophage is preferably specific for a particular species of mycobacteria. Most preferably the mycobacteriophage is selected from the group consisting of lytic mycobacteriophages L29, D34, DS-6A.

During infection by mycobacteria the bacteria enter macrophages via receptor-mediated phagocytosis which may involve several mycobacteria-specific receptors on the macrophage membrane. Following initial interaction with receptor(s), the mycobacteria enter the early phagosome, arrest its maturation and sequester it from the terminal phagocytic organelles e.g. lysosomes. This prevents fusion of the infected phagosome with lysosome and subsequent lysosome-directed lysis of the mycobacteria. It is by this mechanism that mycobacteria form an intracellular infection within a vesicle of the macrophage and avoid the host cell's immune system.

Mycobacteria infect monocytes and macrophages. Thus, when selecting a targeting moiety for use in an agent for treating a mycobacterial cell infection, that targeting moiety should bind to a monocyte and/or a macrophage.

Suitable targeting moieties include Bordetella pertussis filamentous haemagglutinin which binds to complement receptor CR3 and can be internalised via a receptor-medicated endocytosis mechanism; complement component C3; antibody to C3 which can form an agent capable of binding to C3 in human sera and directing phage internalisation through the CR3 receptor; and ligands to macrophage receptors specific to mycobacteria (eg. mannose receptor, surfactant protein receptor, CD14 etc) which can bind receptors and be internalised. A transferrin molecule or a part thereof or a mutant or derivative thereof is a preferred targeting moiety. For sequence details of transferrin, reference is made to Uzan, G., Frain, M., Park, I., Besmond, C., Maessen, G., Trepat, G. S., Zakin, M. M., and Kahn, A. (1984) Molecular cloning and sequence analysis of cDNA for human transferrin Biochem Biophys. Res. Commun. 119, 1; 273–281; and Welch, S. (1990) A comparison of the structure and properties of serum transferrin from 17 animal species Comp. Biochem. Physiol.-B 97(3); 417–27.

According to a second aspect of the present invention, there is provided a method for preparing the agent according to the above definitions, comprising contacting the targeting moiety and the phage such that the targeting moiety becomes associated with the phage.

A large stock of phage may be readily produced. Reference is now made to mycobacteriophage production, although similar scale-up procedures would be equally applicable for other phages.

Phage stock may be produced by the infection of a liquid culture of M. tuberculosis or another auxiliary mycobacterium strain, removing cell debris by centrifugation, phage concentration (eg. by membrane filtration, PEG precipitation, centrifugation etc.,) followed by phage purification (eg. by gel filtration, additional membrane filtration etc.) from components (eg. proteins, polypeptides, salts, etc.) which can interfere with its chemical modification. This process can be easily scaled up by using filtration and chromatographic devices with required throughput.

The stock of phage may then be mixed with the targeting moiety of interest.

Transferrin is now illustrated simply as an example of a targeting moiety. The bonding by physical adsorption requires only a mixing of phage and targeting moiety which have sufficiently different isoelectric points (eg. transferrin, which molecule has pI=5.5, and a phage with pI above 7). The Tf-Phage complex appears stable under physiological conditions and it may be easily separated from the free Tf. The presence of free phage can be afforded since it will only enhance the biological activity of the preparation.

According to a third aspect of the present invention, the agent is prepared by bonding a targeting moiety to a phage. Examples of the preferred bonding procedure have been discussed above.

According to a fourth aspect of the present invention, there is provided a chimeric phage capable of causing lysis of a microorganism within a cell, comprising a targeting moiety capable of binding to the cell as part of a tail or coat protein of the phage.

According to a fifth aspect of the present invention there is provided a method for preparing the chimeric phage described above. Mycobacteriophages are illustrated as an example of this aspect of the present invention. Using mycobacteriophages which genomes have been fully sequenced and characterised (eg. phage L5 or d29), primers can be generated to identify DNA domains which encode "functionally silent" surface membrane proteins within the phage of interest. These can be excised and replaced with a DNA domain encoding the receptor binding moiety (eg. binding domain of transferrin). Accordingly, novel "designed" chimeric phages may be produced which combine the replication function and the receptor binding function. Phages can be accumulated as discussed above and used as therapeutic agents against intracellular pathogens.

According to a sixth aspect of the present invention there is provided a composition comprising an agent of the present invention or a chimeric phage of the present invention, and a pharmaceutically acceptable carrier. The composition is preferably a liquid mixture of agent or chimeric phage and stabiliser which will stabilise the phage during storage in a nebuliser. The mixture may also contain another agent that will prevent phage aggregation.

Many intracellular infections caused by microorganisms are contracted by inhalation Many such intracellular infections are therefore concentrated in and around lung tissues. In particular, tuberculosis (caused by M. tuberculosis) is contracted in this manner. According to preferred embodiment, the composition according to the present invention is provided in an aerosol form.

Reference is now made to the following examples.

Example 1

Modified Lytic Anti-M. tuberculosis Phage as an Agent for the Treatment of Tuberculosis.

This example describes the preparation of a lytic anti-M. tuberculosis phage (phage D34) that was modified either by absorption or chemically to carry a surface polypeptide that provides phage binding, internalisation and delivery into the phagosome within infected monocytes/macrophages. Once within the phagosome, the phage displays its lytic characteristics and either damages or lyses intraphagosomal mycobacteria.

When human monocyte/macrophage cells U937 infected with M. phlei were treated with a sample of modified phage (columns 3 and 4 in Table 1), the number of alive intracellular mycobacteria plated from macrophage lysates was less as compared to that from lysates without phage treatment or treatment with a non-modified phage (columns 5 and 2 in Table 1). The strongest effect was achieved when the targeting moiety (transferrin) was added to, a phage by physical absorption. As the result of a physical modification, phage was two-fold more effective as compared to non-modified phage. The latter level is known to be at least equal to the best result achieved with antibiotics, eg. isoniazid.

These in vitro data demonstrate that phage modification with a specific delivery targeting moiety enhance phage capability to reduce bacterial load within infected macrophages. The phage therapy with modified phage can be efficient against *M. tuberculosis* infection and will help the immune system to neutralise and control the infection and, eventually, tuberculosis.

TABLE 1

The Effect of Transferrin (Trf)-modified and non-modified phage on U937 infection with *Mycobacterium phlei.*

| Phage | Phage, −Trf | Phage, +nMTrf | Phage, +Trf | No Phage |
|---|---|---|---|---|
| Titre (1/ml) | $8.4 \times 10^6$ | $4.4 \times 10^3$ | $4.3 \times 10^4$ | — |
| Viable cells (1/ml) | 422 | 222 | 377 | 638 |
| Viable cells/ Viable cells (−Phage) | 0.66 | 0.34 | 0.59 | 1.0 |

Differentiated U937 cells were used ($4.8 \times 10^5$ cells/ml, 98% alive)

The above *M. phlei*-infected monocyte/macrophages in example 1 were suspended for 1 hour in RPMI media containing gentamycin 4 mg/ml, washed 3 times with PBS and resuspended in RPMI prior to treatment with the modified phage. This was to ensure that surface bound or released *M. phlei* bacteria (ie. non-intracellular mycobacteria) did not mask the result of the example.

What is claimed is:

1. A mycobacteriophage that includes a ligand associated with the mycobacteriophage, wherein the ligand is a transferrin molecule, or a fragment thereof that binds to a transferrin receptor on a macrophage or monocyte, and wherein following binding of the ligand to the macrophage or monocyte the mycobacteriophage enters the macrophage or monocyte and effects lysis of a microorganism residing within the macrophage or monocyte.

2. The mycobacteriophage of claim 1, wherein the microorganism is a bacterium.

3. The mycobacteriophage of claim 2, wherein the bacterium is *Mycobacterium tuberculosis.*

4. The mycobacteriophage of claim 1, wherein the mycobacteriophage is selected from the group consisting of L29, D34 and DS-6A.

5. A method of preparing the mycobacteriophage of claim 1, comprising contacting a ligand, which is a transferrin molecule or a fragment thereof that binds to a transferin receptor on a macrophage or monocyte, with a mycobacteriophage such that the ligand becomes associated with the mycobacteriophage.

6. A method of preparing the mycobacteriophage of claim 1, comprising bonding a ligand, which is a transferrin molecule or a fragment thereof that binds to a transferin receptor on a macrophage or monocyte, to a mycobacteriophage.

7. A composition comprising the mycobacteriophage of claim 1, and a pharmaceutically acceptable carrier.

8. The composition of claim 7 for aerosol delivery.

9. A method of treating an intracellular infection by a microorganism, comprising administering to a patient an effective amount of a mycobacteriophage according to claim 1, wherein the mycobacteriophage enters the macrophage or monocyte and effects lysis of the microorganism residing within the macrophage or monocyte.

10. A mycobacteriophage that includes a ligand associated with the mycobacteriophage, wherein the ligand is a transferrin molecule or a fragment thereof that binds to a transferrin receptor on the surface of a macrophage or monocyte said ligand being exogenous with respect to the mycobacteriophage, and wherein following binding of the ligand to the macrophage or monocyte the mycobacteriophage enters the macrophage or monocyte and effects lysis of a microorganism residing within the macrophage or monocyte.

* * * * *

UNITED STATES PATENT AND TRADEMARK OFFICE
CERTIFICATE OF CORRECTION

PATENT NO.    : 6,660,264 B1
DATED         : December 9, 2003
INVENTOR(S)   : Pasechnik et al.

It is certified that error appears in the above-identified patent and that said Letters Patent is hereby corrected as shown below:

<u>Column 10,</u>
Lines 12 and 18, please delete "transferin" and insert therein -- transferrin --.

Signed and Sealed this

Thirteenth Day of July, 2004

JON W. DUDAS
*Acting Director of the United States Patent and Trademark Office*